United States Patent [19]

Umezawa et al.

[11] 4,060,682

[45] Nov. 29, 1977

[54] PROCESS FOR THE SYNTHETIC PRODUCTION OF 3-DEOXY DERIVATIVE OF AN AMINOGLYCOSIDIC ANTIBIOTIC

[75] Inventors: Hamao Umezawa; Sumio Umezawa, both of Tokyo; Osamu Tsuchiya, Yokohama; Eiichi Akita, Kamakura; Takeo Miyazawa, Tokyo; Yukio Horiuchi, Yokohama; Shunzo Fukatsu, Tokyo, all of Japan

[73] Assignee: Meiji Seika Kaisha, Ltd., Tokyo, Japan

[21] Appl. No.: 598,379

[22] Filed: July 23, 1975

[30] Foreign Application Priority Data

Aug. 1, 1974 Japan .................................. 49-87499

[51] Int. Cl.$^2$ ....................... A61K 31/71; C07H 15/22
[52] U.S. Cl. ..................................... 536/10; 424/180; 536/12; 536/14; 536/17
[58] Field of Search ................... 260/210 AB, 210 K; 536/10, 17

[56] References Cited

U.S. PATENT DOCUMENTS 3,868,360  2/1975  Daniels et al. ................. 260/210 AB

OTHER PUBLICATIONS

Pigman "The Carbohydrates", 1957, Academic Press Inc., New York, N. Y., pp. 390-395.

Primary Examiner—Johnnie R. Brown
Attorney, Agent, or Firm—Haight & Huard

[57] ABSTRACT

3'-Deoxy derivatives of neamine, 6'-N-alkylneamine, kanamycin B, 6'-N-alkylkanamycin B, ribostamycin, 6'-N-alkylribostamycin and paromamine may be produced by a new process comprising reducing the 3',4'-α-anhydro derivative (namely, the 3',4'-epoxide derivative) of the aminoglycosidic antibiotics with hydrogen in an alkaline lower alkanol medium containing an alkali metal hydroxide or alkoxide dissolved therein and in the presence of a reducing catalyst such as Raney nickel. The 3',4'-α-anhydro derivative may be prepared by treating the 3'-sulfonylated derivative of the amino-protected and hydroxyl-protected neamine, 6'-N-alkylneamine, kanamycin B, 6'-N-alkylkanamycin B, ribostamycin, 6'-N-alkylribostamycin or paromamine with an alkali metal hydroxide or alkoxide in a lower alkanol to effect epoxidation between the 4'-hydroxyl group and the carbon atom substituted by the 3'-sulfonic ester group.

17 Claims, No Drawings

PROCESS FOR THE SYNTHETIC PRODUCTION OF 3-DEOXY DERIVATIVE OF AN AMINOGLYCOSIDIC ANTIBIOTIC

This invention relates to a new process for the synthetic production of 3'-deoxy derivatives of an aminoglycosidic antibiotic. More particularly, this invention relates to a process for the production of known 3'-deoxy derivatives of neamine, a 6'-N-alkyl-neamine, kanamycin B, a 6'-N-alkyl-kanamycin B; ribostamycin, a 6'-N-alkyl-ribostamycin, and paromamine.

3'-Deoxyneamine and a 6'-N-alkyl-3'-deoxyneamine, represented by the general formula (I):

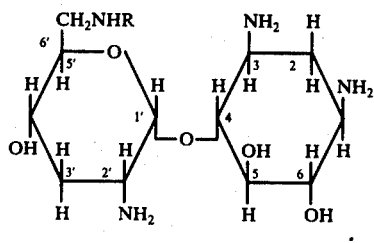

wherein R is a hydrogen atom or an alkyl group, particularly an alkyl group of 1-4 carbon atoms such as methyl, are known (see Belgian Pat. No. 808,393 registered on Dec. 28, 1973 and "Deutsch Offenlegungsschrift" (DT-OS) 2,361,159 published on June 20, 1973). 3'-Deoxykanamycin B and a 6'-N-alkyl-3'-deoxy-kanamycin B represented by the general formula (II):

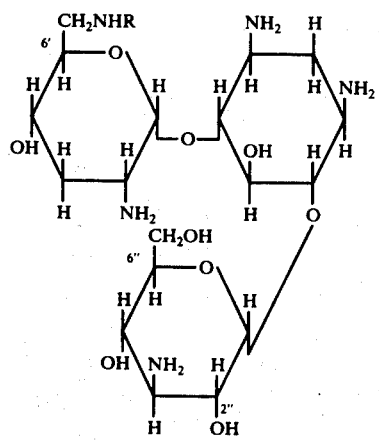

wherein R is a hydrogen atom or an alkyl group, particularly an alkyl group of 1-4 carbon atoms such as methyl, are also known (see the above-mentioned Belgian patent and DT-OS). 3'-Deoxyribostamycin and a 6'-N-alkyl-3'-deoxyribostamycin represented by the general formula (III):

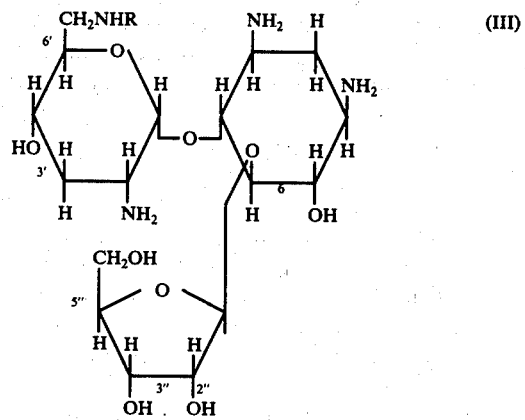

wherein R is a hydrogen atom or an alkyl group, particularly an alkyl group of 1-4 carbon atoms such as methyl, is known (see the above-mentioned Belgian patent and DT-OS). 3'-Deoxyparomamine of the formula (IV):

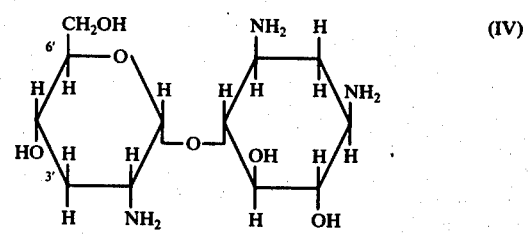

is also known (see, for example, "Journal of Antibiotics" Vol. 24, No. 5. pages 503–510 (1971)).

These compounds 3'-deoxyneamine, 6'-N-alkyl-3'-deoxyneamine, 3'-deoxykanamycin B, 6'-N-alkyl-3'-deoxy-kanamycin B, 3'-deoxyribostamycin, 6'-N-alkyl-3'-deoxy-ribostamycin and 3'-deoxyparomamine may generically be represented by the following general formula (V):

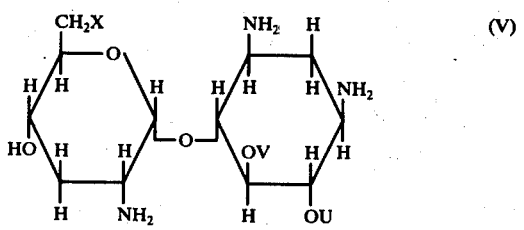

wherein U is hydrogen or 3-amino-3-deoxy-α-D-glucopyranosyl; V is hydrogen or β-D-ribofuranosyl; X is hydroxyl or an amino group of the formula —NHR wherein R is hydrogen or an alkyl group such as alkyl of 1-4 carbon atoms, provided that when X is hydroxyl, both of U and V are hydrogen, and provided that when X is an amino group of the formula —NHR as defined above and when U is 3-amino-3-deoxy-α-D-glucopyranosyl, V is not β-D-ribofuranosyl.

The 3'-deoxy derivatives of aminoglycosidic antibiotics of the aforesaid formulae (I), (II) and (III) exhibit a low toxicity but a markedly higher antibacterial activity against a wide variety of resistant bacteria and *Pseudomonas aeruginosa*, as compared to their parent substances (neamine, kanamycin B and ribostamycin), so that they are useful for therapeutic purposes. 3'-Deoxyparomamine of the formula (IV) is useful as an intermediate for use in the production of semisynthetic antibiotics. Umezawa et al have already proposed a process for the synthetic production of the 3'-deoxy derivatives of aminoglycosidic antibiotics of the formulae (I), (II) and (III) as disclosed in the aforesaid Belgian Pat. No. 808,393 and DT-OS 2,361,159.

In accordance with this prior process proposed by Umezawa et al, an aminoglycosidic antibiotic selected from the group consisting of neamine, kanamycin B and ribostamycin (which may also be called vistamycin) is employed as the starting material, all the amino groups of the starting aminoglycoside employed are blocked with a known amino-protecting group, and a part of the hydroxyl groups other than the 3'- and 4'-hydroxyl groups of the starting aminoglycoside is protected with known hydroxyl-protecting groups to prepare an amino-protected and hydroxyl-protected aminoglycoside derivative. This amino-protected and hydroxyl-protected aminoglycoside derivative is subsequently reacted with an alkylsulfonyl chloride, benzylsulfonyl chloride or an arylsulfonyl chloride to effect a selective sulfonylation of the 3'-hydroxyl group, whereby there is prepared a 3'-sulfonylated derivative of neamine represented by the formula (VI):

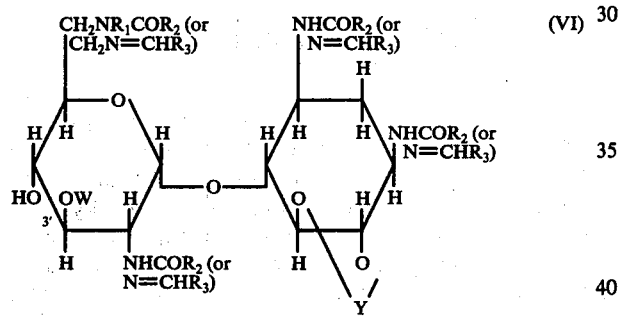

or a 3'-sulfonylated derivative of kanamycin B represented by the formula (VII):

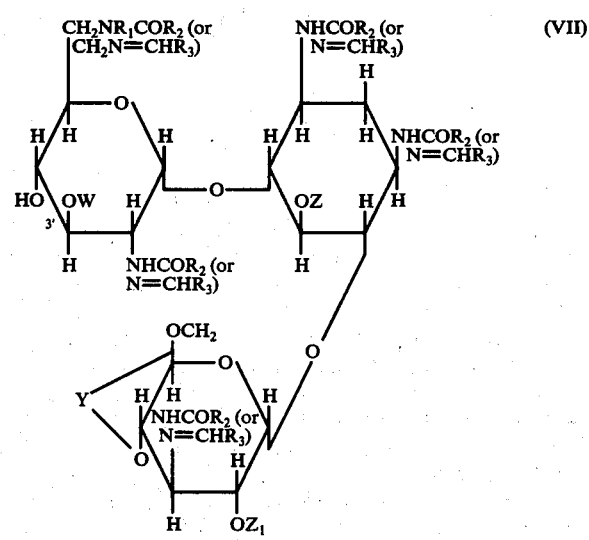

or a 3'-sulfonylated derivative of ribostamycin represented by the formula (VIII):

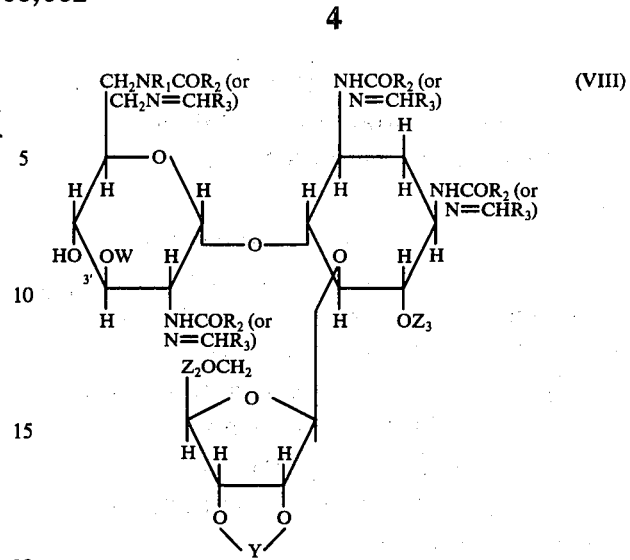

wherein $R_1$ is a hydrogen atom or an alkyl group; $R_2$ is a hydrogen atom or an alkyl group, an aryl group, an alkoxyl group, an aryloxy group or an arylmethoxy group; $R_3$ is a hydrogen atom or an alkyl group or an aryl group; Y is a di-valent hydroxyl-protecting group of the formula

where P and P' each stand for a hydrogen atom or an alkyl group or an aryl group, or Y is cyclohexylidene group or tetrahydropyranyl

group; Z is a hydrogen atom or an acyl group such as benzoyl; $Z_1$ is a hydrogen atom or an acyl group such as benzoyl or an arylmethyl group; $Z_2$ is an acyl group such as acetyl or an arylmethyl group; $Z_3$ is a hydrogen atom or an acyl group such as acetyl or an arylmethyl group; and W is an alkylsulfonyl group such as mesyl, benzylsulfonyl or an arylsulfonyl group such as tosyl. The 3'-sulfonic ester group (—OW) of the 3'-sulfonylated derivative (VI), (VII) or (VIII) so prepared is then reacted with an alkali metal bromide such as sodium bromide or an alkali metal iodide such as sodium iodide to effect the 3'-bromination or 3'-iodination, and the resulting 3'-bromination or 3'-iodination product is converted into the corresponding 3'-deoxy compound by reducing said product with hydrogen in the presence of a hydrogenation catalyst such as Raney nickel, followed by removing the residual protecting groups. In this known synthetic process, it is also possible for the aforesaid 3'-sulfonylated derivative to be directly converted into the corresponding 3'-deoxy compound by reducing the 3'-sulfonylated derivative with a metal hydride such as aluminum lithium hydride.

However, it must be admitted that the abovementioned known synthetic process is disadvantageous in that it involves relatively many stages of reaction, that when a metal hydride is employed as a reagent, the use of relatively expensive aluminum lithium hydride is unavoidable in practice, and that the drastic reactivity of aluminum lithium hydride can necessitate the use of a completely anhydrous reaction medium or solvent and render troublesome the operation of that stage where aluminum lithium hydride is reacted with the aforesaid 3'-sulfonylated derivative (VI), (VII) or (VIII).

We, the present inventors, have made our research in an attempt to develop an improved process for the synthetic production of the 3'-deoxy derivatives of aminoglycosidic antibiotics, which can be operated with a fewer number of reaction stages and under more moderate reaction conditions than the above-mentioned known synthetic process. As a result, we have now found that when the 3'-sulfonylated derivative of the aforesaid formula (VI), (VII) or (VIII) is treated with a lower alkanol of 1-4 carbon atoms such as methanol, ethanol, n-propanol, isopropanol, n-butanol or isobutanol containing an alkali metal hydroxide such as lithium hydroxide, potassium hydroxide and sodium hydroxide or an alkali metal lower alkoxide of 1-4 carbon atoms such as potassium methylate, potassium ethylate, sodium methylate and sodium ethylate which is present in an amount sufficient to make the alkanol medium alkaline, the 3'-sulfonic ester group (—OW) and the 4'-hydroxyl group (which may have been acylated in the form of a 4'-acyloxy group such as benzoyloxy group) of said 3'-sulfonylated derivatives are reacted with each other to form a single epoxide group, so that said 3'-sulfonylated derivative is converted into the corresponding 3',4'-α-anhydro (or 3',4'-α-epoxide) compound. We have also found that when said epoxide group so formed is reduced in such a particular manner that this reduction is effected with hydrogen in the presence of a skeleton catalyst such as Raney catalyst and especially Raney nickel catalyst and within an alkaline reaction medium consisting of a lower alkanol of 1-4 carbon atoms containing an amount of an alkali metal hydroxide or an alkali metal alkoxide as mentioned above, the epoxide group is ring-fissioned so that the 3'-position is deoxygenated (namely, the original 3'-hydroxyl group is removed) and the 4'-hydroxyl group is concurrently restored in the original configuration or orientation. The present invention is based on the above-mentioned findings.

According to this invention, therefore, there is provided an improved process for the production of a 3'-deoxy derivative of an aminoglycosidic antibiotic selected from 3'-deoxyneamine, a 6'-N-alkyl-3'-deoxyneamine, 3'-deoxykanamycin B, a 6'-N-alkyl-3'-deoxykanamycin B, 3'-deoxyribostamycin, a 6'-N-alkyl-3'-deoxyribostamycin and 3'-deoxyparomamine and represented by the aforesaid general formula (V), which comprises a. a step of reducing with hydrogen a 3',4'-α-anhydro derivative of aminoglycoside selected from the group consisting of (i) a 3',4'-α-anhydro derivative of neamine or 6'-N-alkylneamine represented by the formula

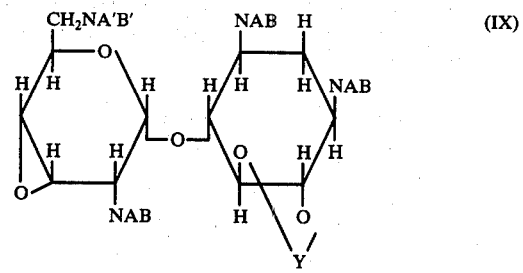

wherein either A and B are each a hydrogen atom; or A is a hydrogen atom and B is a known mono-valent amino-protecting group; or A and B taken together form a known di-valent amino-protecting group; and either A' and B' are each a hydrogen atom; or A' is an alkyl group and B' is a hydrogen atom; or A' is a hydrogen atom and B' is a known mono-valent amino-protecting group; or A' is an alkyl group and B' is a known mono-valent amino-protecting group; or A' and B' taken together form a known di-valent amino-protecting group; and Y is a known di-valent hydroxyl-protecting group or represents two separate hydrogen atoms so that the two hydroxyl groups to which Y is attached remain unprotected (ii) a 3',4'-α-anhydro derivative of kanamycin B or 6'-N-alkylkamycin B represented by the formula (X):

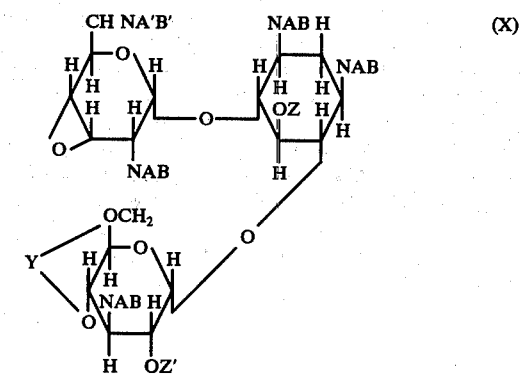

wherein A, B, A', B' and Y have the same meanings as defined above, respectively, Z is a hydrogen atom or an acyl group, and Z' is a hydrogen atom or a known hydroxyl-protecting group of the arylmethyl type, (iii) a 3',4'-α-anhydro derivative of ribostamycin or 6'-N-alkylribostamycin represented by the formula (XI):

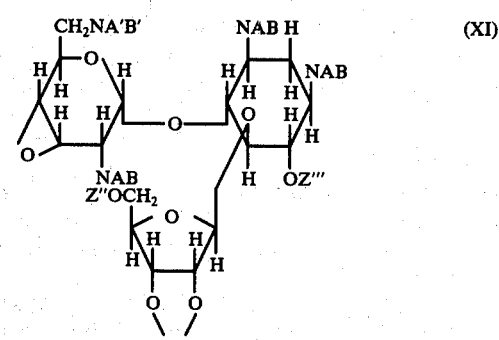

wherein A, B, A', B' and Y have the same meanings as defined above, respectively; Z" is a hydrogen atom or a known hydroxyl-protecting group of the arylmethyl type; and Z''' is a hydrogen atom or a known hydroxyl-protecting group of the arylmethyl type, and (iv) a 3',4'-α-anhydro derivative of paromamine represented by the formula (XII):

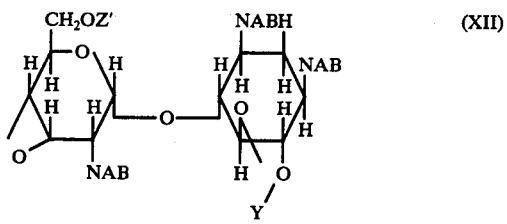

wherein A, B, Y and Z' have the same meanings as defined above, respectively, in an alkaline reaction medium consisting of a lower alkanol containing an alkali metal hydroxide or alkoxide and in the presence of a skeleton catalyst to effect the ring-fissioning of the 3',4'-α-epoxide group, involving the 3'-deoxygenation and concurrent formation of the 4'-α-hydroxyl group, and b. a step of removing the residual protecting groups in a known manner from the 3'-deoxygenation product obtained in the reaction stage (a).

With respect to the 3',4'-α-epoxy compounds of the formula (IX), (X), (XI) or (XII), when B is a known mono-valent amino-protecting group, this amino-protecting group may preferably be an acyl group, an alkoxycarbonyl group, an aryloxycarbonyl group or an arylmethoxycarbonyl group which are respectively represented by the formula —$COR_2$ where $R_2$ is as defined hereinbefore, that is, a hydrogen atom, an alkyl group, an aryl group such as phenyl, an alkoxyl group, an aryloxy group such as phenoxy, or an arylmethoxy group such as benzyloxy. When B is a known di-valent amino-protecting group, this protecting group may preferably be an alkylidene or arylidene group represented by the formula =$CHR_3$ where $R_3$ is as defined hereinbefore, that is, a hydrogen atom, an alkyl group or an aryl group such as phenyl. The hydroxyl-protecting group Y may preferably be a group of the formula

wherein P and P' are each a hydrogen atom or an alkyl group and particularly an alkyl group of 1-4 carbon atoms such as methyl, ethyl, propyl or butyl; or an aryl group such as phenyl, p-methoxyphenyl or o-hydroxypenyl; or alternatively the group Y may preferably be cyclohexylidene or tetrahydropyranyl group. When Z is a hydroxyl-protecting group of the acyl type, the group Z may preferably be an alkanoyl group of 2-5 carbon atoms, for example, acetyl, propionyl or butyryl group. When the groups Z', Z" and Z''' are a hydroxyl-protecting group of the acyl type, respectively, these groups may preferably be an alkanoyl group of 2-5 carbon atoms or an aroyl group such as benzoyl group. When the groups Z', Z" and Z''' are a hydroxyl-protecting group of the arylmethyl type, it may preferably be benzyl.

The starting 3', 4'-α-epoxy compound of the formula (IX), (X) or (XI) may be prepared in the following way. Thus, neamine, kanamycin B, ribostamycin or paromamine or a 6'-N-alkyl derivative thereof (of which preparation is described in the specification of British Pat. No. 1,384,221 and Japanese patent application pre-publication No. 41345/74) is employed as the initial material, and all of the functional amino groups of the initial material are protected in a manner known per se in the conventional synthesis of polypeptides by reacting said initial material with such a reagent which is usually used to block functional amino groups with a known amino-protecting group. All or part of the functional hydroxyl groups other than the 3'-hydroxyl groups of the amino-protected initial material so prepared is then protected with a known hydroxyl-protecting group in a manner known per se in the conventional synthesis of polypeptides, by reacting with such a reagent which is usually employed to block a functional hydroxyl group with said known hydroxyl-protecting group, so that an amino-protected and partly hydroxyl-protected derivative of the initial material employed is afforded. This amino-protected and partly hydroxyl-protected derivative so obtained is subsequently reacted with an alkylsulfonylating, benzylsulfonylating or arylsulfonylating reagent of the formula (XIII):

$R_4SO_2Cl$ or Br     (XIII)

wherein $R_4$ is an alkyl group, particularly an alkyl group of 1-4 carbon atoms, for example, methyl or ethyl group; or a benzyl group; or an aryl group such as phenyl or p-tolyl, at a temperature of up to 50° C to selectively sulfonylate the 3'-hydroxyl group of the amino-protected and partly hydroxyl-protected derivative of the initial material. The preparation of the above-mentioned amino-protected and partly hydroxyl-protected derivative of neamine, kanamycin B or ribostamycin and the subsequent, selective 3'-sulfonylation thereof are described in detail in the specification of the aforesaid Belgian Pat. No. 808,393 and DT-OS 2,361,159.

Through the above-mentioned selective 3'-sulfonylation, there is prepared (i) an amino-protected and partly hydroxyl-protected 3'-sulfonylated derivative of neamine or a 6'-N-alkylneamine represented by the formula (IX'):

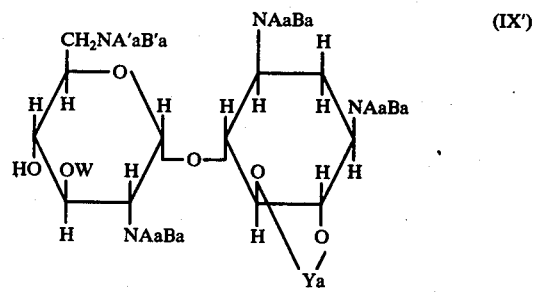

wherein Aa is a hydrogen atom and Ba is a known mono-valent amino-protecting group; or Aa and Ba taken together form a known di-valent amino-protecting group; A'a is an alkyl group and B'a is a hydrogen atom, or Aa is a hydrogen atom and B'a is a known mono-valent amino-protecting group, or A'a is an alkyl group and B'a is a known mono-valent amino-protecting group, or A'a and B'a taken together form a known di-valent amino-protecting group; W is an alkylsulfonyl group, benzylsulfonyl group or an arylsulfonyl group of the formula —$SO_2R_4$; and Ya is a known di-valent hydroxyl-protecting group, (ii) an amino-protected and partly hydroxyl-protected 3'-sulfonylated derivative of kanamycin B or a 6'-N-alkylkanamycin B represented by the formula (X');

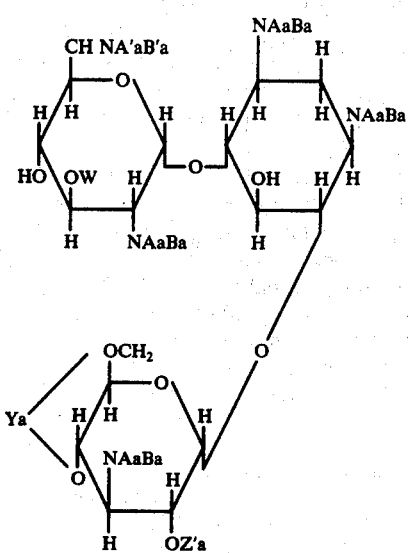

wherein Aa, Ba, A'a, B'a, W and Ya have the same meanings as defined above, respectively, and Z'a is a hydrogen atom or a known hydroxyl-protecting group of the acyl or arylmethyl type, (iii) an amino-protected and partly hydroxyl-protected 3'-sulfonylated derivative of ribostamycin or a 6'-N-alkylribostamycin represented by the formula (XI'):

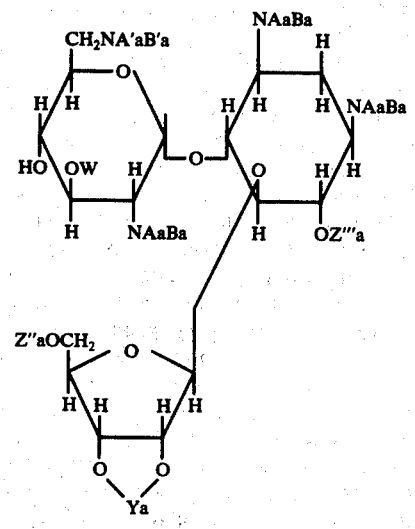

wherein Aa, Ba, A'a, B'a, W and Ya have the same meanings as defined above, respectively, Z"a is a known hydroxyl-protecting group of the acyl type or arylmethyl type, and Z'''a is a hydrogen atom or a known hydroxyl-protecting group of the acyl type or the arylmethyl type, or (iv) an amino-protected and partly hydroxyl-protected 3'-sulfonylated derivative of paromamine represented by the formula (XII'):

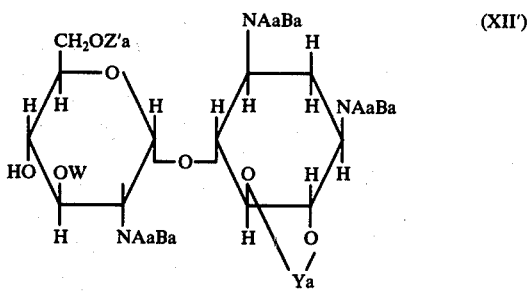

wherein Aa, Ba, W, Ya and Z'a have the same meanings as defined above. With the amino-protected and hydroxyl-protected 3'-sulfonylated derivative (IX'), (X'), (XI') or (XII'), all the amino groups thereof have been protected and all or a part of the hydroxyl groups other than 3'- and 4'-hydroxyl groups have been protected. If desired, all or part of the amino-protecting groups as well as all or part of the hydroxyl-protecting groups may subsequently be removed from the amino-protected and hydroxyl-protected 3'-sulfonylated derivative (IX'), (X'), (XI') or (XII') by treating this protected 3'-sulfonylated derivative in a conventional manner for the removal of the protecting groups, giving a partly or wholly unprotected 3'-sulfonylated derivative, before the conversion of the protected 3'-sulfonylated derivative (IX'), (X'), (XI') or (XII') into the 3',4'-α-anhydro derivative (that is, the 3',4'-α-epoxide derivative) is effected. If desired, it is also possible that the 4'-hydroxyl group of the protected 3'-sulfonylated derivative (IX'), (X'), (XI') or (XII') may be acylated with an alkanoyl group of 2–5 carbon atoms such as acetyl, propionyl or butyryl, by reacting with the corresponding alkanoic acid anhydride or chloride. The 4'-alkanoyl derivative so prepared from the protected 3'-sulfonylated derivative (IX'), (X') (XI') or (XII') also may subsequently be converted into the corresponding 3',4'-α-anhydro derivative.

The protected 3'-sulfonylated derivative (IX'), (X'), (XI') or (XII') (including the partly or wholly unprotected derivative thereof and the 4'-alkanoyl derivative thereof) may be epoxidated to the corresponding 3',4'-α-anhydro derivative (the 3',4'-α-epoxide derivative), by dissolving the 3'-sulfonylated compound (IX'), (X'), (XI') or (XII') in a volume of a lower alcohol of 1–4 carbon atoms such as methanol or ethanol, admixing the resulting alcoholic solution with an alkali metal hydroxide or alkoxide, for example, sodium methylate, in an amount sufficient to render said alcoholic solution alkaline and stirring the resultant admixture at ambient temperature or at an elevated temperature, so that the carbon atom substituted by the 3'-sulfonic ester group (—OW) reacts with the 4'-hydroxyl group (or possibly the 4'-alkanoyl group) to form the 3',4'-α-epoxy group. When the resulting reaction mixture is admixed with a volume of water, the desired epoxide product deposits as a precipitate and may be collected as a crude product by filtration. This crude epoxide product need not be purified and may immediately be used as the starting material in the process of this invention. When the protected 3'-sulfonylated derivative (IX'), (X'), (XI') or (XII') which are employed to prepare the 3',4'-α-anhydro derivative (that is, the 3',4'-α-epoxide derivative) contains the hydroxyl-protecting group of the acyl type for the value of the groups Z'a, Z"a, Z"'a, these acyl groups can be removed (and thus, the values of the groups Z'a, Z"a and Z'''a are converted into a hydrogen atom, respectively) during the process of the conversion of said protected 3'-sulfonylated derivative into the 3',4'-α-anhydro derivative, because the deacylation takes place owing to the alkaline reaction conditions involved in the epoxidation reaction of preparing said 3',4'-α-anhydro derivative in such a manner that the deacylation reaction preceeds or occurs concurrently with the epoxidation reaction. The reaction mixture containing the 3',4'-α-anhydro derivative (IX), (X), (XI) or (XII) formed may immediately be employed as the charge material for the process of the present invention without isolating said 3',4'-α-anhydro derivative therefrom and may be reduced with hydrogen in the presence of a skeleton catalyst according to the process of the present invention.

According to an embodiment of this invention, therefore, the process of this invention comprises further a stage of preparing a hydroxyl-protected and amino-protected 3',4'-α-anhydro derivative of neamine or 6'-N-alkylneamine represented by the aforesaid formula (IX); a hydroxyl-protected and amino-protected 3',4'-α-anhydro derivative of kanamycin B or 6'-N-alkylkanamycin B represented by the aforesaid formula (X); a hydroxyl-protected and amino-protected 3',4'-α-anhydro derivative of ribostamycin or 6'-N-alkylribostamycin represented by the aforesaid formula (XI); or a hydroxyl-protected and amino-protected 3',4'-α-anhydro derivative of paromamine represented by the aforesaid formula (XII), by treating an amino-protected and partly hydroxyl-protected 3'-sulfonylated derivative of neamine or 6'-N-alkylneamine represented by the aforesaid formula (IX'); an amino-protected and partly hydroxyl-protected 3'-sulfonylated derivative of kanamycin B or 6'-N-alkylkanamycin B represented by the aforesaid formula (X'); an amino-protected and partly hydroxyl-protected 3'-sulfonylated derivative of ribostamycin or 6'-N-alkylribostamycin represented by the aforesaid formula (XI'); or an amino-protected and partly hydroxyl-protected 3'-sulfonylated derivative of paromamine of the formula (XII'), in a lower alkanol with an alkali metal hydroxide or alkoxide in an amount sufficient to render said alkanol alkaline to effect the epoxidation between the carbon atom substituted by the 3'-sulfonic ester group (—OW) and the 4'-hydroxyl group, and then, if desired or required, removing a part or all of the amino-protecting groups as well as a part or all of the hydroxyl-protecting groups from the resulting 3',4'-α-epoxide product and, if desired, protecting an unprotected hydroxyl group of said resulting 3',4'-α-epoxide product with a known hydroxyl-protecting group.

In the process of this invention, the 3'-deoxylation step, that is, the step of reducing the starting 3',4'-α-anhydro derivative of the formula (IX), (X), (XI) or (XII) into the corresponding 3'-deoxy compound, is carried out using hydrogen in the presence of a skeleton catalyst, a lower alkanol as the reaction medium and an amount of an alkali metal hydroxide or alkoxide. The lower alkanol available for this purpose may be, for example, methanol, ethanol, n-propanol, isopropanol n-butanol or isobutanol etc., but methanol and ethanol are most preferred. The lower alkanol medium should be made alkaline by dissolving therein a sufficient amount of an alkali metal hydroxide, for example, the hydroxide of an alkali metal such as lithium, potassium and sodium, or alternatively an alkoxide, for example, a lower alkoxide such as the methylate and ethylate of an alkali metal such as lithium, potassium and sodium. It is then preferable that the amount of an alkali metal hydroxide or alkoxide dissolved in the lower alkanol should be 0.5 to 15% by weight of the alcohol. The skeleton catalyst employed in the process acts as a hydrogenation catalyst and may generally be a Raney catalyst. Raney nickel catalyst and Raney cobalt catalyst are especially suitable. The skeleton catalyst may preferably be present in an amount of 0.5-50% by weight of the weight of the lower alkanol employed. The reduction reaction may preferably be conducted at ambient temperature using gaseous hydrogen at atmospheric or higher pressure. The gaseous hydrogen may be diluted with an inert gas such as nitrogen or argon, if desired. Although the reduction time depends on the reaction time, the reaction pressure, the proportion of the skeleton catalyst and other various operating factors, it may generally be 5 to 20 hours. After the catalytic reduction, the reaction mixture is freed from the catalyst by filtration and the filtrate is concentrated to give a residue comprising a crude 3'-deoxygenation product which has been formed through the fission of the 3', 4'-α-epoxide ring of the starting material of the formula (IX), (X), (XI) or (XII). If the resulting 3'-deoxygenation product still contains the residual amino-protecting group and/or the hydroxyl-protecting group, these residual protecting groups are removed in a conventional manner, for example, as described in the aforesaid Belgian Pat. No. 808,393 and DT-OS 2,361,159. Suitable methods for removing the residual protective groups may be chosen by the skilled in the art, depending on the nature of the protective groups remaining in the 3'-deoxygenation product. In this way, the desired 3'-deoxy derivative of the aminoglycosidic antibiotic of the formula (I), (II), (III), (IV) or (V) can be obtained according to the process of this invention, and it may conveniently be purified chromatographically using a weak cation-exchange resin such as Amberlite CG 50.

With such a cycloaliphatic compound containing two adjacent hydroxyl groups positioned in a trans-relationship to each other, one of which has been O-sulfonylated and the other of which is either in the free state or has been acylated, it is known that this cycloaliphatic compound may generally be converted into the corresponding epoxy derivative by treating with an alkali and thereby bringing about the interaction between the carbon atom substituted by the O-sulfonylated hydroxyl group and the free or acylated hydroxyl group to form the epoxy group (see Andre Rosowsky's "Heterocyclic Compounds" 19, Part I, page 153, published by Interscience Publishers, 1964). The epoxy derivative so produced bears the epoxy ring at the side where, among the two hydroxyl groups of the starting cycloaliphatic compound, there is positioned in the same manner as that of the one hydroxyl group which has initially not been sulfonylated.

The epoxidation reaction mentioned just above may take place with a variety of sugar compounds (see the above publication "Heterocylic Compounds" 19, Part I, pages 151, 152, 154, 155, 156, 157 and 158). However, the epoxidation reaction of this type has never been applied scientifically nor commercially in the field of amino-sugar compounds to which the desired 3'-deoxy derivatives of aminoglycosidic antibiotics to be produced according to this invention belong. In particular, it is to be noted that the epoxidation reaction of this type has never been applied to aminoglycosidic antibiotics.

It is known that when an epoxide is ring-fissioned by any reductive reaction, there is usually produced a monohydric alcohol. Which one of the two carbon atoms to which the two hydroxyl groups of the initial trans-dihydric alcohol (from which has been derived the epoxide compound) are attached corresponding to the carbon atom of the monohydric alcohol to which the single hydroxyl group of said monohydric alcohol is bonded depends largely on the nature of the protecting group employed, possible steric hindrance involved by the protecting group, the influence of the protecting group on the electron distribution in the molecule as observed from the view-point of electron theory, and the nature of the reducing agent employed. Therefore, it mainly depends on the above-mentioned various factors, whether the steric configuration of the one hydroxyl group among the two hydroxyl groups of the initial trans-dihydric alcohol is retained or reversed in the molecule of the monohydric alcohol product which is formed through the ring fission of the epoxy group of the epoxy derivative as derived from said trans-dihydric alcohol (see the above-mentioned publication "Heterocyclic Compounds" pages 198 and 217). In these circumstances, it will be expected that when the 3'-O-alkylsulfonylated, 3'-O-arylsulfonylated or 3'-O-benzylsulfonylated compounds which have been formed from the amino-protected and hydroxyl-protected derivative of the particular aminoglycosidic antibiotics would be subjected to the epoxidation reaction and the subsequent reduction with hydrogen similar to the process of this invention, these 3'-O-alkylsulfonylated, 3'-O-arylsulfonylated or 3'-O-benzylsulfonylated compounds would be converted into a deoxy compound via the epoxy compound, but it can never be predicted that this deoxy compound is selectively deoxylated at its 3'-position while the initial steric configuration of the adjacent 4'-hydroxyl group is retained in the resulting deoxy compound. By selecting the particular reaction conditions for the reduction step, that is, the 3'-deoxygenation step as stipulated according to this invention, we have succeeded to selectively deoxygenate the 3'-position of the initial aminoglycosidic antibiotics via the 3'-sulfonylated compound and via the 3',4'-α-epoxy compound derived from the initial aminoglycosidic antibiotic, which ensuring that the original steric configuration of the adjacent 4'-hydroxyl group thereof is retained in the ultimate 3'-deoxylation product.

As compared to one embodiment of the prior method of Belgian Pat. No. 808,393 or DT-OS 2,361,159 which is performed via the 3'-iodinated or 3'-brominated intermediate product, the process of this invention is advantageous in that the number of reaction stages involved in the process of this invention may be reduced by one. This is because the process of this invention is carried out in such a manner that the epoxy compound of the formula (IX), (X), (XI) or (XII) is produced from the 3'-O-alkylsulfonylated, 3'-O-arylsulfonylated or 3'-benzylsulfonylated compound of the formula (IX'), (X'), (XI') or (XII'), the isolation of the epoxy compound from the reaction mixture may be omitted and the epoxy compound may be immediately reduced with hydrogen to give the 3'-deoxylation product, whereas the isolation of the 3'-iodinated or 3'-brominated intermediate is not avoidable in the prior method of the Belgian Patent or DT-OS. Furthermore, the process of this invention may be performed via the epoxidation step and the reduction step which are both carried out under moderate reaction conditions, and in this respect the process of this invention is advantageous over the prior method of the aforesaid Belgian Patent or DT-OS.

As compared to the other embodiment of the prior method of the aforesaid Belgian Pat. No. 808,393 or DT-OS which is performed using a metal hydride as the reducing reagent, the process of this invention is performable under more moderate reaction conditions and is commercially advantageous in this respect. The prior method of the aforesaid Belgian Patent or DT-OS usually employs aluminum lithium hydride for the metal hydride and is carried out under drastic reaction conditions owing to the high reactivity of aluminum lithium hydride, and besides it is troublesome in that it needs the use of completely anhydrous solvent. In these respects, the prior method of the aforesaid Belgian patent or DT-OS is disadvantageous as compared to the process of this invention.

3'-Deoxyneamine, 3'-deoxy-6'-N-methylneamine, 3'-deoxyribostamycin, 3'-deoxy-6'-N-methylribostamycin, 3'-deoxykanamycin B, 3'-deoxy-6'-N-methylkanamycin B and 3'-deoxyparomamine which are produced by the process of this invention have been confirmed to be identical to their authentic samples, respectively, by making comparison between their n.m.r. spectra (in $D_2O$), mass spectra of their derivatives, thin layer chromatography on silica gel (developed with 4:5:2:5 n-butanolethanol-chloroform-17% aqueous ammonia) and antibacterial spectra. These 3'-deoxy derivatives of the aminoglycosidic antibiotics which are obtained by the process of this invention, excepting 3'-deoxyparomamine, exhibit not only an activity inhibitory to the growth of resistant *Staphylococcus aureus*, resistant *Escerichia coli* and resistant *Pseudomonas aeruginosa* as shown in Table 1 below, but also an activity inhibitory to the growth of *Klebsiella pneumonia*, *Diplococcus pneumonia* and *Salmonella typhosa*. These 3'-deoxy derivatives are of low toxicity similarly to their parent substances and are useful for the therapeutic treatment of infections by gram-positive and gram-negative bacteria. 3'-Deoxyparomamine is useful as an intermediate for synthesis of any valuable derivative of aminoglycosidic antibiotics. The minimum inhibitory concentrations (mcg/ml) of these 3'-deoxy derivatives against various microorganisms were determined according to a standard serial dilution method using nutrient agar incubation medium at 37° C, the estimation being effected after 18 hours incubation. The results so obtained are shown in Table 1 below.

Table 1

| | Minimum Inhibitory Concentration (mcg/ml) | | | | |
|---|---|---|---|---|---|
| Test Microorganism | 3'-Deoxy-neamine | 3'-Deoxy-ribostamycin | 3'-Deoxy-kanamycin B | 3'-Deoxy-6'-N-methyl-kanamycin B | 3'-Deoxy-paromamine |
| *Staphylococcus aureus* FDA 209P | 3.12 | 6.25 | 0.78 | 1.56 | 50 |
| *Escherichia coli* K12 | 6.25 | 6.25 | 0.78 | 0.78 | 100 |
| *Escherichia coli* K12 ML1629 | 6.25 | >100 | 0.78 | 1.56 | 100 |
| *Escherichia coli* K12 ML1410 | 6.25 | 6.25 | 0.78 | 1.56 | >100 |
| *Escherichia coli* K12 LA290 R55 | 100 | >100 | 50 | 50 | 50 |
| *Escherichia coli* K12 W677 | 6.25 | 3.12 | 1.56 | 1.56 | >100 |

Table 1-continued

| Test Microorganism | Minimum Inhibitory Concentration (mcg/ml) | | | | |
|---|---|---|---|---|---|
| | 3'-Deoxy-neamine | 3'-Deoxy-ribostamycin | 3'-Deoxy-kanamycin B | 3'-Deoxy-6'-N-methyl-kanamycin B | 3'-Deoxy-paromamine |
| *Escherichia coli* K12 JR66/W677 | >100 | >100 | 50 | 50 | >100 |
| *Pseudomonas aeruginosa* A3 | 6.25 | 3.12 | 0.78 | 0.78 | >100 |
| *Pseudomonas aeruginosa* No.12 | 6.25 | 3.12 | 0.78 | 0.78 | >100 |
| *Pseudomonas aeruginosa* GN315 | >100 | >100 | 100 | 6.25 | >100 |

The invention is now illustrated with reference to the following Examples to which the invention is not limited in any way.

EXAMPLE 1

Synthesis of 3'-deoxykanamycin B a. 2''-O-Benzoyl-penta-N-ethoxycarbonyl-4'',6''-O-cyclohexylidene-3'-O-tosylkanamycin B (1.0 g) (described in Example 1 of the Belgian Pat. No. 808,393 or DT-OS 2,361,159) was dissolved in 50 ml of ethanol and the resulting solution was admixed with 5 ml of a solution of 28% sodium methylate in methanol. The resultant admixture was allowed to stand for 1 hour at ambient temperature to effect the epoxidation and concurrent removal of the 2''-O-benzoyl group, and a portion was taken as a sample from the reaction mixture so obtained. Analysis of this sample confirmed the presence of penta-N-ethoxycarbonyl-4'',6''-O-cyclohexylidene-3',4'-epoxy($\alpha$)-kanamycin B in the reaction mixture.

b. This reaction mixture was admixed with 10 ml of a commericaly available Raney nickel catalyst, and the mixture was subjected to catalytic reduction with gaseous hydrogen at atmospheric pressure and at ambient temperature for 6 hours under stirring. The reaction mixture was then filtered to remove the Raney nickel, and the filtrate was concentrated by evaporation of the solvent.

c. The solid residue so obtained was analyzed for a sample taken therefrom, and it was confirmed that this residue contained penta-N-ethoxycarbonyl-4'',6''-O-cyclohexylidene-3'-deoxykanamycin B. This residue was admixed with 25 ml of acetic acid and 12 ml of water, and the admixture was heated for 1.5 hours under reflux, whereby the removal of the cyclohexylidene group was effected. The reaction solution so obtained was then concentrated to dryness and the solid residue was admixed with 25 g of barium hydroxide and 33 ml of water. The admixture was heated for 15 hours under reflux, whereby the removal of the ethoxycarbonyl group was effected. The reaction solution so obtained was neutralized by passing thereinto a stream of carbon dioxide gas and was then filtered to remove the precipitate of barium carbonate formed. The filtrate was passed through a column of 30 ml of a cation-exchange resin Amberlite CG50 (NH$_4$+ form) to make the 3'-deoxykanamycin B product, adsorb onto the cation-exchange resin. The cation-exchange resin column was then eluted with 0.15 N to 0.35 N aqueous ammonia. The eluate was collected in 10 ml fractions, the fraction Nos. 21 to 31 were combined together and the combined solution was concentrated to dryness under reduced pressure to give 129 mg of a crude product of 3'-deoxykanamycin B. This crude product was chromatographically purified by passing an aqueous solution of this crude product through a column of 30 ml of Amberlite CG50 (NH$_4$+ form) and then eluting the resin column with 0.15 N to 0.35 N aqueous ammonia. The eluate was collected in 5 ml fractions and the fraction Nos. 45 to 63 were combined together and concentrated to dryness under reduced pressure, affording 99 mg of 3'-deoxykanamycin B. Yield 24%.

$[\alpha]_D$ +126° ($c$ 1.0, H$_2$O)

Elemental analysis

Calculated for C$_{18}$H$_{37}$N$_5$O$_9$.H$_2$O: C44.53, H 8.10, N 14.43% Found: C 44.25, H 8.28, N 14.43%

EXAMPLE 2

Synthesis of 3'-deoxyribostamycin a. 2'',3''-O-cyclohexylidene-tetra-N-ethoxycarbonyl-5'',6-diacetyl-3'-O-tosylribostamycin (1.0 g) (described as 5'',6-di-O-acetyl-tetra-N-ethoxycarbonyl-2'',3''-O-cyclohexylidene-3'-O-tosylvistamycin in Example 1 of the Belgian Pat. No. 808,393 or DT-OS 2,361,159) was dissolved in 45 ml of ethanol and the resulting solution was admixed with 4.5 ml of a solution of 28% potassium methylate in methanol. The resultant admixture was allowed to stand for 1 hours at ambient temperature to effect the epoxidation and concurrent removal of the acetyl groups, and a portion was taken as a sample from the reaction mixture so obtained. Analysis of this sample confirmed the presence of 2'',3''-O-cyclohexylidene-tetra-N-ethoxycarbonyl-3',4'-epoxy($\alpha$)-ribostamycin in the reaction mixture.

b. This reaction mixture was admixed with 9 ml of a commercially available Raney nickel catalyst, and the mixture was subjected to catalytic reduction with gaseous hydrogen at atmospheric pressure and at ambient temperature for 7 hours under agitation. The reaction mixture was then filtered to remove the Raney nickel, and the filtrate was concentrated to dryness.

c. The solid residue so obtained was analyzed from a sample taken out therefrom, and it was confirmed that this residue contained 2'',3''-O-cyclohexylidene-tetra-N-ethoxycarbonyl-3'-deoxyribostamycin. This residue was admixed with 25 ml of acetic acid and 12.5 ml of water, and the admixture was heated for 1.5 hours under reflux, whereby the removal of the cyclohexylidene group was effected. The reaction solution was then concentrated to dryness under reduced pressure, and the solid residue was admixed with 24 g of barium hydroxide and 32 ml of water. The admixture was heated for 15 hours under reflux, whereby the removal of the ethoxycarbonyl group was effected. The reaction solution so obtained was neutralized by passing therein a stream of gaseous carbon dioxide and was then filtered to remove the precipitate of barium carbonate formed. The filtrate was passed through a column of 25 ml of Amberlite CG50 (NH$_4$+ form) to make the 3'-deoxyribostamycin product adsorb onto the cation-exchange resin. The cation-exchange resin column was then eluted with 0.15 N to 0.35 N aqueous ammonia. The eluate was collected in 10 ml fractions, the fraction Nos. 10 to 21 were combined together and the combined solution was concentrated to dryness under reduced pressure to give 120 mg of a crude product of 3'-deoxyribostamycin. This crude product was chromatographically purified by passing an aqueous solution of this crude product through a column of 25 ml of Amberlite CG50 ($NH_4^+$ form) and then eluting the resin column with 0.15 N to 0.35 N aqueous ammonia. The eluate was collected in 5 ml fractions, and the fraction Nos. 22 to 43 were combined together. The combined solution was concentrated to dryness under reduced pressure, affording 40 mg of 3'-deoxyribostamycin. Yield 9.7%. $[\alpha]_D$ +33° (c 1.0, $H_2O$).

EXAMPLE 3

Synthesis of 3'-deoxyneamine a. Tetra-N-ethoxycarbonyl-5,6-O-cyclohexylidene-3'-O-tosylneamine (600 mg) (described in Example 5 of the Belgian Pat. No. 808,393 or DT-OS 2,361,159) was dissolved in 45 ml of ethanol, and the resulting solution was admixed with a solution of 28% sodium methylate in methanol. The mixture so obtained was allowed to stand for 30 minutes at ambient temperature to effect the epoxidation. The reaction mixture was admixed with 500 ml of water, and a white precipitate deposited was filtered off from said reaction mixture. This precipitate was washed with water and dried to give 460 mg of a crude product of tetra-N-ethoxycarbonyl-5,6-O-cyclohexylidene-3',4'-epoxy($\alpha$)-neamine. This product did not show any signal attributable to the tosyl group upon a N.M.R. spectrum analysis and did not give any acetylated derivative thereof when it was subjected to an ordinary O-acetylation method using acetic anhydride in pyridine.

b. The crude tetra-N-ethoxycarbonyl-5,6-O-cyclohexylidene-3',4'-epoxy($\alpha$)-neamine (400 mg) was dissolved in 30 ml of ethanol and the resulting solution was made alkaline by addition of 3 ml of a solution of 28% sodium methylate in methanol. The mixture so obtained was subjected to catalytic reduction with hydrogen gas at an elevated pressure of 3 atm. and at ambient temperature in the presence of 6 ml of a commercially available Raney nickel catalyst added thereto. The catalytic reduction was effected for 7 hours under agitation, and the reaction mixture was filtered to remove the Raney nickel. The filtrate was concentrated by evaporation of the solvent to give a solid residue.

c. The residue was analyzed for a sample taken out therefrom, and it was confirmed that the residue contained tetra-N-ethoxycarbonyl-5,6-O-cyclohexylidene-3'-deoxyneamine. This residue was admixed with 12 ml of acetic acid and 6 ml of water, and the admixture was heated for 1.5 hours at 110° C under reflux, whereby the removal of the cyclohexylidene group was effected. The reaction slution was then concentrated to dryness under reduced pressure, and the solid residue was admixed with 12 g of barium hydroxide and 16.5 ml of water. The admixture was heated for 15 hours under reflux, whereby the removal of the ethoxycarbonyl group was effected. The reaction solution so obtained was then neutralized by passing therein a stream of carbon dioxide gas and was then filtered to remove the precipitate of barium carbonate formed. The filtrate was passed through a column of 15 ml of Amberlite CG50 ($NH_4^+$ form) to make the 3'-deoxyneamine product adsorb onto the cation-exchange resin. The resin column was then eluted with 0.15 N to 0.4 N aqueous ammonia, and the eluate was collected in 10 ml fractions. The fraction Nos. 8 to 17 were combined together and the combined solution was concentrated to dryness under reduced pressure to give 85 mg of a crude product of 3'-deoxyneamine. This crude product was purified by chromatography in a column of 20 ml of Amberlite CG50 ($NH_4^+$ form) with 0.2 N to 0.4 N aqueous ammonia as the development solvent in the same manner as stated above. Thus, the eluate was collected in 5 ml fractions, and the fraction Nos. 15 to 33 were combined together and concentrated to dryness under reduced pressure to give 35 mg of 3'-deoxyneamine. Yield 13.2%. $[\alpha]_D$ +101° (c 1.0, $H_2O$)

EXAMPLE 4

Synthesis of 3'-deoxykanamycin B a. 2''-O-benzoyl-penta-N-benzyloxycarbonyl-4'',6''-O-cyclohexylidene-3'-O-tosylkanamycin B (407 mg) [which was prepared from 2''-O-benzoyl-3',4'; 4'',6''-di-O-cyclohexylidene-penta-N-salicylidenekanamycin B (described in Example 1(a) (iii) of the Belgian Pat. No. 808,393 or DT-OS 2,361,159) by subjecting the latter kanamycin B derivative to the process of Example 1(a) (iv) using benzyl chloroformate in place of ethoxycarbonyl chloride, followed by sulfonylating with tosyl chloride in a similar manner to Example 1(b) of said Belgian patent or DT-OS] was dissolved in a mixture of 12 ml of dioxane, 17 ml of water and 2 ml of acetic acid. The resulting solution was subjected to catalytic reduction with hydrogen gas at atmospheric pressure and at ambient temperature for 6 hours in the presence of an amount of palladium-black catalyst added thereto, whereby the removal of the benzyloxycarbonyl group was effected. The reaction mixture so obtained was filtered to remove the palladium catalyst, and the filtrate was concentrated. The concentrated filtrate containing 2''-benzoyl-4'',6''-O-cyclohexylidene-3'-O-tosylkanamycin B acetate was admixed with 15 ml of aqueous 80% acetic acid and the admixture was heated at 65° C for 3 hours, whereby the removal of the cyclohexylidene group was effected. The reaction mixture so obtained was neutralized by addition of an amount of sodium methylate and then concentrated to a smaller volume. The concentrated residue was taken up into 8 ml of ethanol and admixed with 0.8 ml of a solution of 28% sodium methylate in methanol. The resulting admixture was allowed to stand for 1 hour at ambient temperature to effect the epoxidation and concurrent removal of the 2''-O-benzoyl group. From the reaction mixture so obtained a portion thereof was taken as a sample. Analysis of this sample showed that 3',4'-epoxy($\alpha$)-kanamycin B was present in said reaction mixture.

b. After addition of 1 ml of a commercially available Raney nickel catalyst, the reaction mixture was subjected to catalytic reduction with hydrogen gas at atmospheric pressure and at ambient temperature. The catalytic reduction was conducted for 6 hours under agitation and the reaction mixture was filtered to remove the catalyst. The filtrate was neutralized by addition of acetic acid and then passed through a column of 4 ml of Amberlite CG50 ($NH_4^+$ form) to make the 3'-deoxykanamycin B product adsorb onto the cation-exchange resin. The resin column was eluted with 0.15 N to 0.35 N aqueous ammonia and the eluate was collected in 1 ml fractions. Fraction Nos. 28 to 37 were combined and concentrated to dryness to obtain a crude product of 3'-deoxykanamycin B. This crude product was chromatographically purified in the same manner as in Example 1(c). Yield 2%.

EXAMPLE 5

Synthesis of 3'-deoxyparomamine a. Tri-N-ethoxycarbonylparomamine (100 mg) was dissolved in 0.1 ml of a mixture of pyridine-benzeneacetic anhydride (10:10:1 by volume) and the solution was allowed to stand at 25° C for 5 hours to effect the acetylation. The reaction solution was admixed with 5 ml of cold water, and the precipitate comprising tri-N-ethoxycarbonyl-6'-O-acetylparomamine deposited was filtered out. This tri-N-ethoxycarbonyl-6'-O-acetylparomamine product was treated with 1,1-dimethoxy cyclohexane and then with tosyl chloride in a manner substantially the same as described in Example 1(a) and (b) of the Belgian Pat. No. 808,393 and DT-OS 2,361,159 to give 30 mg of tri-M-ethoxycarbonyl-6'-O-acetyl-5,6-O-cyclohexylidene-3'-tosylparomamine. This substance was dissolved in 2 ml of ethanol and the resulting ethanolic solution was admixed with 0.2 ml of a solution of 28% sodium methylate in methanol. The admixture so obtained was allowed to stand for 30 minutes at ambient temperature to effect the epoxidation and concurrent removal of the 6'-O-acetyl group. The reaction mixture was admixed with 20 ml of water and the white precipitate deposited was removed by filtration. The precipitate was washed with water and dried to give 18 mg of a crude product of tri-N-ethoxycarbonyl-5,6-O-cyclohexylidene-3',4'-epoxy($\alpha$)-paromamine.

b. This crude product (15 mg) was dissolved in 1 ml of ethanol and the resulting solution was made alkaline by admixing with 0.1 ml of a solution of 28% sodium methylate in methanol. The admixture so obtained was subjected to catalytic reduction with hydrogen gas at a pressure of 2 atm. and at ambient temperature for 6 hours in the presence of 0.2 ml of a commercially available Raney nickel catalyst. The reaction mixture was filtered to remove the Raney nickel, and the filtrate was concentrated.

c. A portion was taken as a sample from the concentrated solution so obtained, and analysis of this sample showed that said concentrated solution contained tri-N-ethoxycarbonyl-5,6-cyclohexylidene-3'-deoxyparomamine. The concentrated solution was admixed with 1 ml of acetic acid and 0.5 of water and the admixture was heated at 110° C for 1.5 hours, hereby the removal of the cyclohexylidene group was effected. The reaction solution was concentrated to dryness and the solid residue was admixed with 0.5 g of barium hydroxide and 0.6 ml of water, and the resulting admixture was heated for 10 hours under reflux, whereby the removal of the ethoxycarbonyl group was effected. The liquid reaction mixture was neutralized with carbon dioxide gas, and a precipitate of barium carbonate deposited was filtered off. The filtrate (2 ml) was passed through a column of 2 ml of Amberlite CG50 (type II) ($NH_4^+$ form) to make the 3'-deoxyparomamine product adsorb onto the cation-exchange resin. The resin column was eluted with 0.1 N to 0.2 N aqueous ammonia, and the eluate was collected in 1 ml fractions. The fraction Nos. 8 to 13 were combined together and concentrated to dryness to give 5 mg of a crude product of 3'-deoxyparomamine. This crude product was chromatographically purified in a column of Amberlite CG50 ($NH_4^+$ form) using 0.1 N to 0.2 N aqueous ammonia as the development solvent in the same manner as described above. 3'-deoxyparomamine was obtained in a yield of 3 mg.

EXAMPLE 6

Synthesis of 3'-deoxy-6'-N-methylkanamycin B a. 2''-O-benzoyl-penta-N-ethoxycarbonyl-4'',6''-O-cyclohexylidene-3'-O-tosyl-6'-N-methylkanamycin B (1.0 g) [which was obtained by reacting 1.2 g of 6'-N-methylkanamycin B (described in the "Journal of Antibiotics" Vol. 25, No. 12, pages 743–745, December, 1972 and in Japanese patent application pre-publication No. 41345/74 published on Apr. 18, 1974) successively with salicylaldehyde, 1,1-dimethoxycyclohexane, benzoyl chloride, aqueous acetic acid, ethoxycarbonyl chloride and tosyl chloride in the same manner as described in Example 1(a), (b) of the Belgian Pat. No. 808,393 or DT-OS 2,361,159] was dissolved in 50 ml of ethanol and the resulting solution was admixed with 5 ml of a solution of 28% sodium methylate in methanol. The admixture was obtained was allowed to stand for 1 hour at ambient temperature to effect the epoxidation and concurrent removal of the 2''-O-benzoyl group. A portion was taken out as a sample from the reaction mixture and analyzed, and it was then observed that the reaction mixture contained penta-N-ethoxycarbonyl-4'',6''-O-cyclohexylidene-3',4'-epoxy($\alpha$)-6'-N-methylkanamycin B.

b. This reaction mixture was admixed with 10 ml of a commercially available Raney nickel catalyst and then subjected to catalytic reduction with hydrogen gas at atmospheric pressure and at ambient temperature. The catalytic reduction was conducted for 6 hours under agitation. The reaction mixture so obtained from the catalytic reduction was filtered to remove the Raney nickel, and the filtrate was concentrated.

c. The concentrated filtrate so obtained was analyzed for a sample taken out therefrom, and it was shown that this concentrated solution contained penta-N-ethoxycarbonyl-4'',6''-O-cyclohexylidene-3'-deoxy-6'-N-methylkanamycin B. The concentrated solution was admixed with 25 ml of acetic acid and 12 ml of water, and the resulting admixture was heated for 1.5 hours under reflux, whereby the removal of the cyclohexylidene group was effected. The reaction solution so obtained was then concentrated to dryness and the solid residue was mixed with 25 g of barium hydroxide and 33 ml of water, followed by heating for 15 hours under reflux, whereby the removal of the ethoxycarbonyl group was effected. The reaction mixture so obtained was neutralized with carbon dioxide gas and the precipitate of barium carbonate formed was filtered off. The filtrate was passed through a column of 30 ml of Amberlite CG50 ($NH_4^+$) to make the 3'-deoxy-6'-N-methylkanamycin B adsorb onto the cation-exchange resin. The resin column was eluted with 0.15 N to 0.35 N aqueous ammonia, and the eluate was collected in 10 ml fractions. The fraction Nos. 25 to 40 were combined together and the combined solution was concentrated to dryness under reduced pressure to give 150 mg of a crude product of 3'-deoxy-6'-N-methylkanamycin B. This crude product was then purified chromatographically in a column of 30 ml of Amberlite CG50 ($NH_4^+$) using 0.15 N to 0.35 N aqueous ammonia as the development solvent in the same manner as stated above. 3'-deoxy-6'-N-methylkanamycin B (85 mg) was obtained in a yield of 4.1%. $[\alpha]_D +121°$ ($c$ 1.0, $H_2O$)

Elemental analysis

Calculated for $C_{19}H_{39}N_5O_9.H_2O$: C, 45.67, H, 8.27, N, 14.02%. Found: C, 45.32, H, 8.09, N, 14.27%.

What we claim is:

1. A compound selected from the group consisting of 3′,4′-α-anhydro derivatives of neamine or 6′-N-alkyl-neamine of the formula:

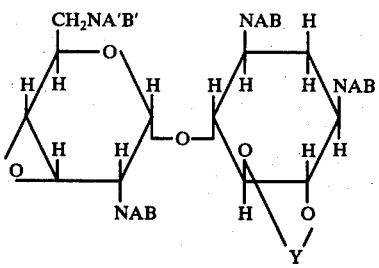

wherein:
A and B are both hydrogen; or A is hydrogen and B is a monovalent amino-protecting group selected from the group consisting of alkanoyl, alkoxycarbonyl, aryloxycarbonyl and arylmethoxycarbonyl of the formula —$COR_2$ wherein $R_2$ is hydrogen, lower alkyl, phenyl, lower alkoxy, phenoxy or benzyloxy; or A and B taken together form a divalent amino-protecting group of the formula >$CHR_3$ wherein $R_3$ is hydrogen, lower alkyl or phenyl;

A′ and B′ are both hydrogen; or A′ is lower alkyl and B′ is hydrogen; or A′ is hydrogen and B′ is a monovalent amino-protecting group selected from the group consisting of alkanoyl, alkoxycarbonyl, aryloxycarbonyl and arylmethoxycarbonyl of the formula —$COR_2$ wherein $R_2$ has the above-indicated values; and Y represents two hydrogen atoms, cyclohexylidene, tetrahydropyranyl or a divalent hydroxyl-protecting group of the formula

wherein P and P′ are each hydrogen, alkyl of 1–4 carbon atoms, phenyl, p-methoxyphenyl or o-hydroxyphenyl.

2. In a process for the preparation of a compound selected from the group consisting of 3′-deoxyneamine and 6′-N-alkyl-3′-deoxyneamine, the improvement which comprises:
catalytically reducing a compound according to claim 1 with hydrogen in an alkaline reaction medium consisting essentially of a lower alkanol solution of alkali metal hydroxide or alkoxide to ring-fission the 3′,4′-α-epoxy group by 3′-deoxygenation with concurrent formation of a 4′-α-hydroxyl group and thereby form a corresponding amino-protected and hydroxyl-protected derivative of 3′-deoxyneamine or 6′-N-alkyl-3′-deoxyneamine.

3. A process according to claim 2, wherein said catalytic reduction is effected at a temperature of from ambient temperature to 40° C. using hydrogen gas at a pressure of 1 to 50 atmospheres and a Raney nickel or Raney cobalt hydrogenation catalyst and wherein said alkali metal hydroxide or alkoxide is present in an amount of 0.5–15% by weight, based on the lower alkanol.

4. A process according to claim 2, wherein said alkaline reaction medium consists essentially of sodium methylate dissolved in ethanol.

5. A compound selected from the group consisting of 3′,4′-α-anhydro derivatives of kanamycin B or 6′-N-alkylkanamycin B of the formula

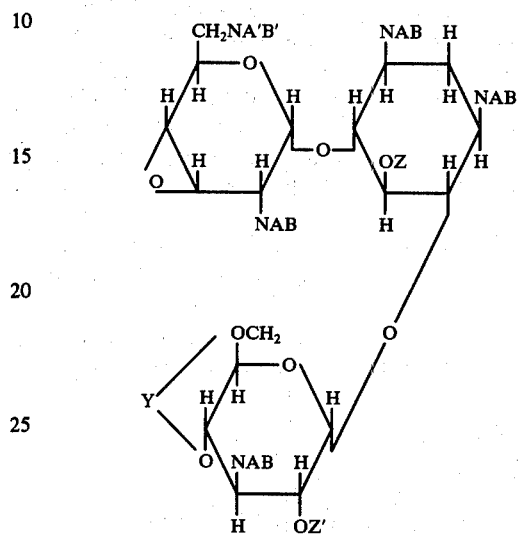

wherein:
A and B are both hydrogen; or A is hydrogen and B is a monovalent amino-protecting group selected from the group consisting of alkanoyl, alkoxycarbonyl, aryloxycarbonyl and arylmethoxycarbonyl of the formula —$COR_2$ wherein $R_2$ is hydrogen, lower alkyl, phenyl, lower alkoxy, phenoxy or benzyloxy; or A and B taken together form a divalent amino-protecting group of the formula >$CHR_3$ wherein $R_3$ is hydrogen, lower alkyl or phenyl;

A′ and B′ are both hydrogen; or A′ is lower alkyl and B′ is hydrogen; or A′ is hydrogen and B′ is a monovalent amino-protecting group selected from the group consisting of alkanoyl, alkoxycarbonyl, aryloxycarbonyl and arylmethoxycarbonyl of the formula —$COR_2$ wherein $R_2$ has the above-indicated values;

Y represents two hydrogen atoms, cyclohexylidene, tetrahydropyranyl or a divalent hydroxyl-protecting group of the formula

wherein P and P′ are each hydrogen, alkyl of 1–4 carbon atoms, phenyl, p-methoxyphenyl or o-hydroxyphenyl;

Z is hydrogen or alkanoyl of 2–5 carbon atoms; and
Z′ is hydrogen alkanoyl of 2–5 carbon atoms or benzyl.

6. In a process for the preparation of a compound selected from the group consisting of 3′-deoxykanamycin B and 6′-N-alkyl-3′-deoxykanamycin B, the improvement which comprises:
catalytically reducing a compound according to claim 5 with hydrogen in an alkaline reaction medium consisting essentially of a lower alkanol solution of alkali metal hydroxide or alkoxide to ring-fission the 3',4'-α-epoxy group by 3'-deoxygenation with concurrent formation of a 4'-α-hydroxyl group and thereby form a corresponding amino-protected and hydroxyl-protected derivative of 3'-deoxykanamycin B and 6'-N-alkyl-3'-deoxykanamycin B.

7. A process according to claim 6, wherein said catalytic reduction is effected at a temperature of from ambient temperature to 40° C. using hydrogen gas at a pressure of 1 to 50 atmospheres and a Raney nickel or Raney cobalt hydrogenation catalyst and wherein said alkali metal hydroxide or alkoxide is present in an amount of 0.5–15% by weight, based on the lower alkanol.

8. A process according to claim 6, wherein said alkaline reaction medium consists essentially of sodium methylate dissolved in ethanol.

9. A compound selected from the group consisting of 3',4'-α-anhydro derivatives of ribostamycin or 6'-N-alkylribostamycin of the formula:

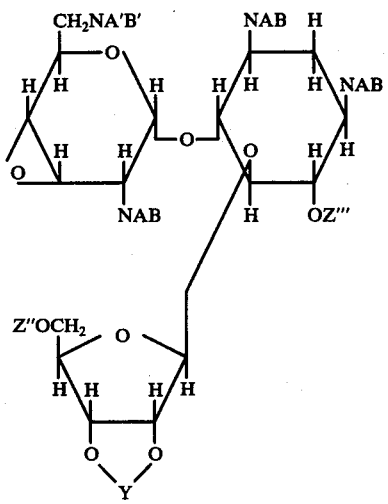

wherein:
A and B are both hydrogen; or A is hydrogen and B is a monovalent amino-protecting group selected from the group consisting of alkanoyl, alkoxycarbonyl, aryloxycarbonyl and arylmethoxycarbonyl of the formula —COR$_2$ wherein R$_2$ is hydrogen, lower alkyl, phenyl, lower alkoxy, phenoxy or benzyloxy; or A and B taken together form a divalent amino-protecting group of the formula >CHR$_3$ wherein R$_3$ is hydrogen, lower alkyl or phenyl;
A' and B' are both hydrogen; or A' is lower alkyl and B' is hydrogen; or A' is hydrogen and B' is a monovalent amino-protecting group selected from the group consisting of alkanoyl, alkoxycarbonyl, aryloxycarbonyl and arylmethoxycarbonyl of the formula —COR$_2$ wherein R$_2$ has the above-indicated values;
Y represents two hydrogen atoms, cyclohexylidene, tetrahydropyranyl or a divalent hydroxyl-protecting group of the formula

wherein P and P' are each hydrogen, alkyl of 1–4 carbon atoms, phenyl, p-methoxyphenyl or o-hydroxyphenyl; and
Z" and Z'" are each hydrogen or benzyl.

10. In a process for the preparation of a compound selected from the group consisting of 3'-deoxyribostamycin and 6'-N-alkyl-3'-deoxyribostamycin, the improvement which comprises:
catalytically reducing a compound according to claim 9 with hydrogen in an alkaline reaction medium consisting essentially of a lower alkanol solution of alkali metal hydroxide or alkoxide to ring-fission the 3',4'-α-epoxy group by 3'-deoxygenation with concurrent formation of a 4'-α-hydroxyl group and thereby form a corresponding amino-protected and hydroxyl-protected derivative of 3'-deoxyribostamycin or 6'-N-alkyl-3'-deoxyribostamycin.

11. A process according to claim 10, wherein said catalytic reduction is effected at a temperature of from ambient temperature to 40° C. using hydrogen gas at a pressure of 1 to 50 atmospheres and a Raney nickel or Raney cobalt hydrogenation catalyst and wherein said alkali metal hydroxide or alkoxide is present in an amount of 0.5–15% by weight, based on the lower alkanol.

12. A process according to claim 10, wherein said alkaline reaction medium consists essentially of sodium methylate dissolved in ethanol.

13. A compound selected from the group consisting of 3',4'-α-anhydro derivatives of paromamine of the formula:

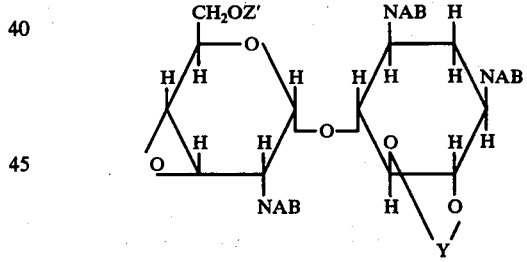

wherein:
A and B are both hydrogen; or A is hydrogen and B is a monovalent amino-protecting group selected from the group consisting of alkanoyl, alkoxycarbonyl, aryloxycarbonyl and arylmethoxycarbonyl of the formula —COR$_2$ wherein R$_2$ is hydrogen, lower alkyl, phenyl, lower alkoxy, phenoxy or benzyloxy; or A and B taken together form a divalent amino-protecting group of the formula >CHR$_3$ wherein R$_3$ is hydrogen, lower alkyl or phenyl;
Y represents two hydrogen atoms, cyclohexylidene, tetrahydropyranyl or a divalent hydroxyl-protecting group of the formula

wherein P and P' are each hydrogen, alkyl of 1–4 carbon atoms, phenyl, p-methoxyphenyl or o-hydroxyphenyl; and Z' is hydrogen alkanoyl of 2–5 carbon atoms or benzyl.

14. In a process for the preparation of a 3'-deoxyparomamine, the improvement which comprises:
catalytically reducing a compound according to claim 13 with hydrogen in an alkaline reaction medium consisting essentially of a lower alkanol solution of alkali metal hydroxide or alkoxide to ring-fission the 3',4'-α-epoxy group by 3'-deoxygenation with concurrent formation of a 4'-α-hydroxyl group and thereby form a corresponding amino-protected and hydroxyl-protected derivative of 3'-deoxyparomamine.

15. A process according to claim 14, wherein said catalytic reduction is effected at a temperature of from ambient temperature to 40° C. using hydrogen gas at a pressure of 1 to 50 atmospheres and a Raney nickel or Raney cobalt hydrogenation catalyst and wherein said alkali metal hydroxide or alkoxide is present in an amount of 0.5–15% by weight, based on the lower alkanol.

16. A process according to claim 14, wherein said alkaline reaction medium consists essentially of sodium methylate dissolved in ethanol.

17. A compound which is selected from the group consisting of tetra-N-ethoxycarbonyl-5,6-O-cyclohexylidene-3',4'-epoxy(α)-neamine; penta-N-ethoxycarbonyl-4'',6''-O-cyclohexylidene-3',4'-epoxy(α)-kanamycin B; 3',4'-epoxy(α)-kanamycin B; penta-N-ethoxycarbonyl-4'',6''-O-cyclohexylidene-3',4'-epoxy(α)-6'-N-methylkanamycin B; 2'',3''-O-cyclohexylidene-tetra-N-ethoxycarbonyl-3',4'-epoxy(α)-ribostamycin; and tri-N-ethoxycarbonyl-5,6-O-cyclohexylidene-3',4'-epoxy(α)-paromamine.

* * * * *